United States Patent
Webster et al.

(10) Patent No.: US 6,403,126 B1
(45) Date of Patent: Jun. 11, 2002

(54) CANNABINOID EXTRACTION METHOD

(75) Inventors: G. R. Barrie Webster, Winnipeg; Leonard P. Sarna, Ste. Anne, both of (CA)

(73) Assignee: Websar Innovations Inc., Ste. Anne (CA)

( * ) Notice: Subject to any disclaimer, the term of this patent is extended or adjusted under 35 U.S.C. 154(b) by 0 days.

(21) Appl. No.: 09/490,457

(22) Filed: Jan. 24, 2000

Related U.S. Application Data

(60) Provisional application No. 60/136,199, filed on May 26, 1999.

(51) Int. Cl.$^7$ ................................................ A61K 35/78
(52) U.S. Cl. ........................................ 424/776; 424/725
(58) Field of Search ............................... 424/195.1, 725, 424/776; 426/651

(56) References Cited

U.S. PATENT DOCUMENTS 4,554,170 A * 11/1985 Panzner et al.

FOREIGN PATENT DOCUMENTS

RU 2103001 * 1/1998

OTHER PUBLICATIONS

Tamiide (Ho Chudoku(Japanese Journal of Forensic Toxicology)), (1998) vol. 16, No. 2, pp. 124–127.*

* cited by examiner

*Primary Examiner*—Christopher R. Tate
*Assistant Examiner*—Randall Winston
(74) *Attorney, Agent, or Firm*—Michael R. Williams; Ryan W. Dupuis; Adrian D. Battison

(57) ABSTRACT

A method of extracting cannabinoids, cannflavins, and/or essential oils from hemp and/or of producing a whole hemp extract lacking $\Delta^9$-THC is herein described. The industrial hemp is harvested and the chaff is threshed from the seeds. The chaff is then ground and the ground chaff is extracted with an organic solvent. The extract is then loaded onto a chromatographic column selected to fractionate specific cannabinoids, cannflavins, and essential oils. In one embodiment, $\Delta^9$-THC is fractionated out of the extract, producing a whole hemp extract lacking $\Delta^9$-THC. In other embodiments, specific cannabinoids and related compounds of interest are fractionated out, thereby producing purified cannabinoids, cannflavins, and related compounds.

14 Claims, No Drawings

US 6,403,126 B1

CANNABINOID EXTRACTION METHOD

This application claims priority under 35 USC §119(e) to Provisional Patent Application Ser. No. 60/136,199 filed on May 26, 1999.

FIELD OF THE INVENTION

The following invention relates generally to the field of methods of chemical purification. More specifically, the present invention relates to a method of producing natural health or medicinal products from Cannabis species, for example, industrial hemp.

BACKGROUND OF THE INVENTION

Recently, public interest in Cannabis as medicine has been growing, based in no small part on the fact that Cannabis has long been considered to have medicinal properties, ranging from treatment of cramps, migraines, convulsions, appetite stimulation and attenuation of nausea and vomiting. In fact, a report issued by the National Academy of Sciences' Institute of Medicine indicated that the active components of Cannabis appear to be useful in treating pain, nausea, AIDS-related weight loss or "wasting", muscle spasms in multiple sclerosis as well as other problems. Advocates of medical marijuana argue that it is also useful for glaucoma, Parkinson's disease, Huntington's disease, migraines, epilepsy and Alzheimer's disease.

Marijuana refers to varieties of Cannabis having a high content of $\Delta^9$-tetrahydrocannabinol ($\Delta^9$-THC), which is the psychoactive ingredient of marijuana whereas industrial hemp refers to varieties of the Cannabis plant that have a low content of $\Delta^9$-THC.

The controversy regarding the medicinal use of marijuana is centered not only on what is delivered but on how it is delivered. Specifically, the primary method used to deliver marijuana into a patient's system is by smoking the marijuana; however, smoking increases an individual's risk for cancer, lung damage and emphysema. Furthermore, as discussed above, marijuana does contain high levels of a psychoactive drug, $\Delta^9$-THC. As such, there has been considerable debate as to whether or not the potential health benefits of smoking marijuana outweigh the health benefits.

However, it is of note that $\Delta^9$-THC is only one of a family of about 60 bi- and tri-cyclic compounds named cannabinoids. These natural products usually contain a 1,1'-dimethyl-pyrane ring, a variedly derivatized aromatic ring and a variedly unsaturated cyclohexyl ring, and include for example the non-psychoactive cannabinol, cannabidiol and cannabinolic acid. These latter compounds have been suggested to contribute to some of the beneficial effects of Cannabis, such as cell protection, immunosuppression and ant-inflammatory properties. This suggests that these non-psychoactive cannabinoids recognize the same cellular receptors as $\Delta^9$-THC but, due to structural differences, do not have the same side effects.

In addition, Cannabis species also contain a related class of compounds, the cannflavins. These natural products usually contain a 1,4-pyrone ring fused to a variedly derivatized aromatic ring and linked to a second variedly derivatized aromatic ring, and include for example the non-psychoactive cannflavins A and B. These compounds have been suggested to contribute some of the beneficial effects of Cannabis, such as analgesia and anti-inflammatory properties, and as such are considerably more effective than aspirin.

Clearly, a process is needed for preparing natural health products containing the non-restricted compounds present in marijuana (and also in industrial hemp) to be used for medicinal purposes.

SUMMARY OF THE INVENTION

According to a first aspect of the invention, there is provided a method of preparing a Cannabis extract comprising:

harvesting Cannabis composed of seed and chaff;

separating the chaff from the seed;

extracting the chaff with a solvent, thereby producing an extract;

passing the extract, if desired, over a chromatographic column arranged to fractionate $\Delta^9$-THC out of the extract; and collecting the fractions lacking $\Delta^9$-THC from the column, thereby producing a whole hemp extract without the $\Delta^9$-THC.

The chaff may be green or dried and the chaff may be ground prior to extraction.

The collected fractions may be concentrated.

The Cannabis may be, for example, industrial hemp.

The solvent may be an organic solvent, selected from the group consisting of: a petroleum derived hydrocarbon, for example, toluene, trimethylpentane; a low molecular weight alcohol, for example, ethanol; a low molecular weight chlorinated hydrocarbon, for example, chloroform and dichloromethane; or a supercritical fluid such as $CO_2$ with or without an organic solvent modifier. Extraction may also occur using a technique referred to as accelerated solvent extraction or may use subcritical water.

According to a second aspect of the invention, there is provided a hemp extract isolated according to the above-described method.

According to a third aspect of the invention, there is provided a pharmaceutical composition comprising the hemp extract according to the abovedescribed method.

According to a fourth aspect of the invention, there is provided a method of extracting a cannabinoid, cannflavin or essential oil from Cannabis comprising:

harvesting Cannabis composed of seed and chaff;

separating the chaff from the seed;

extracting the chaff with a solvent, thereby producing an extract;

passing the extract over a chromatographic column arranged to fractionate the cannabinoid, cannflavin or essential oil of interest out of the extract; and collecting the fractions containing the cannabinoid, cannflavin or essential oil of interest from the column, producing a purified cannabinoid, cannflavin or essential oil. The cannflavins may be cannflavin A or B or other related cannflavin-type compounds.

The cannabinoid may be selected from the group consisting of: cannabidiol (CBD); cannabinol (CBN); cannabigerol (CBG); cannabichromene (CBC); cannabidivarol (CBDV); tetrahydrocannabidiol (THCBD); tetrahydrocannabigerol (THCBG); tetrahydrocannabichromene (THCBC); tetrahydrocannabidivarol (THCBDV); $\Delta^8$-THC; the carboxylic acid precursors of the foregoing compounds; and related naturally occurring compounds and their derivatives.

The chaff may be fresh or dried, and the chaff may be ground prior to extraction.

The collected fractions may be concentrated.

The Cannabis may be for example industrial hemp.

The solvent may be an organic solvent, selected from the group consisting of: a petroleum derived hydrocarbon, for example, toluene, trimethylpentane; a low molecular weight alcohol, for example, ethanol; a low molecular weight chlorinated hydrocarbon, for example, chloroform and dichloromethane; or a supercritical fluid such as $CO_2$ with or without an organic solvent modifier. Extraction may also occur using a technique referred to as accelerated solvent extraction or may use subcritical water.

According to a fifth aspect of the invention, there is provided a purified cannabinoid, cannflavin, or essential oil prepared according to the above-described method.

According to a sixth aspect of the invention, there is provided a pharmaceutical composition comprising the purified cannabinoid, cannflavin or essential oil prepared according the above-described method.

The invention will now be described by way of examples, although the invention is not in any way limited to the examples described herein.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Definitions

As used herein, "industrial hemp" refers to varieties of the Cannabis plant that have a low content of $\Delta^9$-tetrahydrocannabinol ($\Delta^9$-THC).

As used herein, "chaff" refers to the chopped plant material remaining after the seed of the hemp has been harvested and separated by the process known as threshing.

As used herein, "supercritical fluid" refers to materials that are under sufficient pressure and heat that they are no longer distinctly liquid or gaseous.

As used herein, "subcritical water" refers to water that is heated under pressure, but is below its critical point; thus it is still a liquid.

As used herein, "cannabinoids" refers to a family of natural products that usually contain a 1,1'-di-methyl-pyrane ring, a variedly derivatized aromatic ring and a variedly unsaturated cyclohexyl ring and their immediate chemical precursors.

As used herein, "cannflavins" refers to a family of natural products that usually contain a 1,4-pyrone ring fused to a variedly derivatized aromatic ring and linked to a second variedly derivatized aromatic ring.

As used herein, "essential oils" refers to a family of natural products that usually contain a multiple of the 5-membered isoprene unit variedly substituted, often cyclized to form one or more ring systems. They may also contain series of aldehydes and/or ketones and esters of a variety of carboxylic acid substituted compounds.

Described herein is a method of processing Cannabis and extracting cannabinoids, cannflavins or essential oils therefrom. In one embodiment, the extract is run over a column that fractionates $\Delta^9$-tetrahydrocannabinol out of the extract, thereby producing an eluent that is free of $\Delta^9$-THC. The eluent may then be concentrated or otherwise treated by means known in the art to produce a natural health product, that is, a whole hemp extract with the $\Delta^9$-THC removed. In some embodiments, the fractions containing $\Delta^9$-THC may be collected or pooled or the extracted $\Delta^9$-THC may be eluted. In another embodiment, the extract is run over a column arranged to fractionate a specific cannabinoid or class of cannabinoids other than $\Delta^9$-THC. In this embodiment, the fractions containing the cannabinoid, cannflavin or essential oil or class of cannflavins, cannabinoids or essential oils of interest are collected, thereby producing purified cannabinoid(s), cannflavin(s) and/or essential oil(s). Compounds isolated by this method may include but are by no means limited to, for example, cannabidiol (CBD), cannabinol (CBN), cannabigerol (CBG), cannabichromene (CBC), cannabidivarol (CBDV), tetrahydrocannabidiol (THCBD), tetrahydrocannabigerol (THCBG), tetrahydrocannabichromene (THCBC), tetrahydrocannabidivarol (THCBDV), $\Delta^8$-THC, the carboxylic acid precursors of the foregoing compounds, and related naturally occurring compounds and their derivatives. Compounds isolated may also include cannflavins A and B and related compounds. Compounds isolated may also include essential oils and their individual components.

The invention will now be described by way of examples; however, the invention is in no way limited to these examples.

In the example described herein, industrial hemp is harvested and the hemp seeds are threshed from the chaff. The chaff is collected and may then be dried or extracted green. In the embodiment described herein, the chaff is dried and is then finely divided, ground or pulverized. The ground chaff is then extracted with a solvent. In this embodiment, the time of residency of the ground chaff in the solvent is up to approximately 2–4 hours. Furthermore, the mixing ratio of chaff to solvent is such that the chaff can be suspended in the extracting medium during the extraction process. Specifically, in this embodiment the volume ratio is between 10:1 to 100:1. The solvent may be an organic solvent, for example, a petroleum derived hydrocarbon such as for example toluene or trimethylpentane, a low molecular weight alcohol such as for example ethanol, or a low molecular weight chlorinated hydrocarbon such as for example dichloromethane. As will be appreciated by one knowledgeable in the art, other suitable solvents known in the art or combinations thereof may also be used, and the time of residency, volumes and mixing ratios may be varied based upon the cannabinoid(s) to be extracted. In some embodiments, the extract may be concentrated by evaporation of the solvent.

In some embodiments, a supercritical fluid with or without an organic solvent modifier such as methanol may be used as an extractant. As discussed above, supercritical fluids are materials that are under sufficient pressure and heat that they are no longer distinctly liquid or gaseous; as a consequence, they have the penetrating power of gases and the solvating power of liquids. An example of a supercritical fluid is $CO_2$, which is an accessible candidate because it can be made into a supercritical fluid above 32° C. and 73 atmospheres. Furthermore, adjustment of the temperature and pressure can vary the effective polarity of the supercritical fluid. In addition, it is of note that the addition of small quantities of other solvents as modifiers can assist in designing the appropriate solvent for specific target analytes. Thus, the supercritical fluid can be used to extract specific compounds from hemp extract based on their chemical properties. It is of note that other suitable supercritical fluids known in the art may also be used as solvents in some embodiments. It is also of note that accelerated solvent extraction, extraction with subcritical water, or extraction with steam may also be used.

The extract is then passed through a chromatographic column, for example, an HPLC column or a reversed phase HPLC column. In one embodiment, the chromatographic column is arranged for fractioning $\Delta^9$-THC out of the eluent. That is, as the extract is passed over the column, $\Delta^9$-THC is differentially retained or detained on the column. As a result, as the extract comes off the column, the initial fractions eluted off the column will be free of $\Delta^9$-THC. These fractions free of $\Delta^9$-THC are pooled, thereby producing a whole hemp extract with $\Delta^9$-THC removed. In some embodiments, the $\Delta^9$-THC may be eluted from the column, extracted or concentrated, for purifying $\Delta^9$-THC. In alternative embodiments, the chromatographic column is arranged for fractionating a specific cannabinoid, cannflavin or essential oil or class of cannabinoids, cannflavins or essential oils out of the eluent, for example, cannabidiol (CBD), cannabinol (CBN), cannabigerol (CBG), cannabichromene (CBC), cannabidivarol (CBDV), tetrahydrocannabidiol (THCBD), tetrahydrocannabigerol (THCBG), tetrahydrocannabichromene (THCBC), tetrahydrocannabidivarol (THCBDV), $\Delta^8$-THC, the carboxylic acid precursors of the foregoing compounds, and related naturally occurring compounds and their derivatives. In alternate embodiments, the chromatographic column is arranged for fractionating cannflavins A and B and related naturally occurring compounds and their derivatives. In alternate embodiments, the system is arranged to fractionate the components of essential oils. It is of note that the provided list of compounds is by no means exhaustive and is in no way intended to be limiting. In these embodiments, the compound(s) of interest are retained or detained on the column so that the last fractions of the extract eluted from the column contain the compounds(s) of interest. The fractions containing the compound(s) of interest are pooled. In some embodiments, different compounds may be extracted with different solvents and then combined into a single extract. As will be appreciated by one knowledgeable in the art, in this manner, several different cannabinoids could be purified from a single extract.

EXAMPLE I

Extraction Protocol Example

The chaff from the hemp is air dried or dehydrated. The chaff is then pulverized and extracted with agitation in a suitable solvent for a period of time. The solvent may be, for example, ethanol, toluene; or hexane. The liquid extract is then separated from the solid component, for example, by filtration or other means known in the art. At this point, the extract may be concentrated (reduced in volume) or dried and resuspended in a new solvent.

In some embodiments, the foliar and floral material from the hemp may be subjected to supercritical fluid extraction for extracting cannabinoids, cannflavins and/or essential oils. In some embodiments, the supercritical fluid may be $CO_2$ or another supercritical fluid known in the art. In other embodiments, other solvents may be used as modifiers in combination with the supercritical fluid for targeted extraction of specific compounds, as discussed above.

EXAMPLE II

Extraction Protocol Example

Individual components or analytes may be isolated from the above-described extract by subjecting the extract to high pressure liquid chromatography (HPLC) using, for example, a reversed phase $C_{18}$ column and a mobile phase made up of for example acetonitrile and water or methanol and water for the isolation of cannabinoid and cannflavin compounds. For the isolation of the carboxylic analogs, small amounts of, for example, acetic or phosphoric acids are used. For the isolation of the essential oil components, normal phase chromatography may be used with solvents such as hexane, toluene, or ethyl acetate as the mobile phase. Flow rates of for example 0.5 to 3.0 mL/min are used for the analytical separation, 3.0 to 100 mL/min for the preparative isolation on a pilot scale, or 50 to 500 mL/min for full scale production separation.

It is of note that the pooled fractions discussed above may be further concentrated by evaporation to yield extracts which are suitable for further treatment by means known in the art to produce, for example, tinctures, capsules, powders, pills, hemp oil-based or other oil-based capsules, topical applications, creams, salves, gels, drops, lotions, aerosols, sprays, injections and the like. Alternatively, the pooled fractions may be crystallized.

It is of note that the extent to which the chaff is dried can be varied as can the time of storage from harvest of the industrial hemp to extraction of the ground chaff.

It is of note that in some embodiments, the specific cannabinoids isolated are those cannabinoids with suspected health benefits or suspected medicinal uses. For example, the cannabinoids and cannflavins may be used as antiemetics, antinauseants, appetite stimulants, anti-inflammatories, antioxidants, neuroprotectives, analgesics, suppressants for primary immune response, glaucoma remedies, antineoplastics, migraine headache remedies, menstrual pain remedies, anticonvulsants, anti-epileptics, or movement disorder remedies. The essential oils may be used for aromatherapy or as flavoring/scenting adjuvants.

In alternative embodiments, other varieties of Cannabis may be used for extracting cannabinoids.

It is of note that solvent volume may be reduced prior to loading of the extract on the column or after fractionation of the extract. Alternatively, the solvent may be removed prior to loading the extract onto the column or after fractionation and the extract may then be suspended in another suitable solvent, for example, a low molecular weight alcohol.

While the preferred embodiments of the invention have been described above, it will be recognized and understood that various modifications may be made therein, and the appended claims are intended to cover all such modifications which may fall within the spirit and scope of the invention.

What is claimed is:

1. A method of preparing a Cannabis extract comprising:
   harvesting Cannabis composed of seed and chaff;
   separating the chaff from the seed;
   extracting the chaff with a solvent, thereby producing an extract;
   passing the extract over a chromatographic column arranged to fractionate at least one cannabinoid, cannflavin or essential oil out of the extract; and
   collecting the fractions lacking said at least one cannabinoid, cannflavin or essential oil from the column, thereby producing a hemp extract and at least one purified cannabinoid, cannflavin or essential oil.

2. The method according to claim 1 including drying the chaff prior to extraction.

3. The method according to claim 1 including grinding the chaff prior to extraction.

4. The method according to claim 1 including concentrating the collected fractions.

5. The method according to claim 1 wherein the Cannabis is industrial hemp.

6. The method according to claim 1 wherein the solvent is an organic solvent.

7. The method according to claim 28 wherein the organic solvent is selected from the group consisting of: a petroleum derived hydrocarbon; toluene; trimethylpentane, a low molecular weight alcohol; ethanol; a low molecular weight chlorinated hydrocarbon; and dichloromethane.

8. The method according to claim 1 wherein the purified cannabinoid is selected from the group consisting of: $\Delta^9$-THC; cannabidiol (CBD); cannabinol (CBN); cannabigerol (CBG); cannabichromene (CBC); cannabidivarol (CBDV); tetrahydrocannabidiol (THCBD); tetrahydrocannabigerol (THCBG); tetrahydrocannabichromene (THCBC); tetrahydrocannabidivarol (THCBDV); $\Delta^8$-THC; the carboxylic acid precursors of the foregoing compounds; and related naturally occurring compounds and their derivatives.

9. The method according to claim 1 wherein the purified cannflavin is selected from the group consisting of: cannflavin A; cannflavin B; precursors of the foregoing compounds; and related naturally occurring compounds and their derivatives.

10. The method according to claim 1 wherein the extraction is performed using subcritical water.

11. The method according to claim 1 wherein the extraction is performed using steam.

12. The method according to claim 1 wherein the solvent is a supercritical fluid.

13. The method according to claim 12 wherein the solvent includes modifier compounds.

14. The method according to claim 12 wherein the supercritical fluid is $CO_2$.

* * * * *